United States Patent [19]
Aizawa et al.

[11] Patent Number: 6,166,253
[45] Date of Patent: *Dec. 26, 2000

[54] PROCESS FOR PRODUCING N-(1-ALKOXYETHYL)CARBOXYLIC AMIDES

[75] Inventors: Toshiyuki Aizawa; Hitoshi Nakamura; Tetsuo Kudo; Etsuko Mitarai, all of Oita, Japan

[73] Assignee: Showa Denko K.K., Tokyo, Japan

[ * ] Notice: This patent is subject to a terminal disclaimer.

[21] Appl. No.: 09/151,307

[22] Filed: Sep. 11, 1998

Related U.S. Application Data

[63] Continuation of application No. 08/832,667, Apr. 4, 1997, Pat. No. 5,852,214.

[30] Foreign Application Priority Data

Apr. 5, 1996 [JP] Japan .................................... 8-84031

[51] Int. Cl.$^7$ ........................ C07C 231/12; C07C 233/05
[52] U.S. Cl. ........................ 564/215; 564/205; 564/224
[58] Field of Search .................... 564/205, 215, 564/224

[56] References Cited

U.S. PATENT DOCUMENTS 4,554,377 11/1985 Stackman et al. .
4,997,984 3/1991 Sugita et al. .
5,852,214 12/1998 Aizawa et al. .......................... 564/215

FOREIGN PATENT DOCUMENTS 62-289549 12/1987 Japan .
6-100515 4/1994 Japan .

OTHER PUBLICATIONS

Journal of Chemical Society, Chemical Communications, "A New Method for the Synthesis of N–t–Butoxycarbonyl . . . ", pp. 1304–1306, 1990.

*Primary Examiner*—Shailendra Kumar
*Attorney, Agent, or Firm*—Sughrue, Mion, Zinn, Macpeak & Seas, PLLC

[57] ABSTRACT

A process for producing N-(1-alkoxyethyl)carboxylic amides by reacting alcohols of 1-5 carbon atoms with N-vinylcarboxylic amides in the presence of an acidic catalyst, or by utilizing unreacted starting material, unreacted intermediate or unrecovered product for synthesis of N-(1-alkoxyethyl)carboxylic amides. A process for producing N-(1-alkoxyethyl)carboxylic amides by adding a water-soluble strong acid during reaction between a carboxylic amide and a starting material containing acetaldehyde and alcohol and/or a starting material containing an acetal, in an amount of $2 \times 10^{-3}$ to $3 \times 10^{-1}$ equivalents to 1 mole of the carboxylic amide in the starting material, and using a strongly acidic ion-exchange resin as the catalyst.

1 Claim, No Drawings

PROCESS FOR PRODUCING N-(1-ALKOXYETHYL)CARBOXYLIC AMIDES

This is a continuation of application Ser. No. 08/832,667 filed Apr. 4, 1997, now U.S. Pat. No. 5,852,214, the disclosure of which is incorporated herein by reference.

BACKGROUND OF THE INVENTION

1. Field of the Invention

The present invention relates to a process for producing N-(1-alkoxyethyl)carboxylic amides. It specifically relates to a process for producing N-(1-alkoxyethyl)carboxylic amides which are useful for analytical purposes, as intermediates for various agricultural chemicals and medicines, and which are also production intermediates for N-vinylcarboxylic amides which are very useful as monomers for N-vinylcarboxylic amide-based polymers that can be employed in water absorbers and thickeners, and as synthetic materials for chemical agents such as taurine and cysteamine.

The present invention further relates to a process for producing N-vinylcarboxylic amides from N-(1-alkoxyethyl)carboxylic amides, and to a process for producing N-vinylcarboxylic amide-based polymers using the obtained N-vinylcarboxylic amides as monomers.

2. Description of the Related Art

A number of conventional processes have been proposed for synthesizing N-(1-alkoxyethyl)carboxylic amides. Considering the starting materials used in such processes, they may be largely classified into processes using acetals, processes using ethylidene biscarboxylic amides and processes using acetaldehyde.

A process with dimethylacetal as the starting material is disclosed in U.S. Pat. No. 4,554,377 as a process by which dimethylacetal and a carboxylic amide are reacted in the presence of a strong acid such as methanesulfonic acid or sulfuric acid, or a strongly acidic ion-exchange resin. This process, however, has a drawback in that the dimethylacetal must be synthesized separately and isolated for use, while high yields of N-(1-alkoxyethyl)carboxylic amides can only be obtained by diluting the starting composition to a very high degree of 20 moles of dimethylacetal to 1 mole of the carboxylic amide, thus notably lowering productivity. Also, Japanese Unexamined Patent Publication No. 2-009851 describes a process whereby N-(1-alkoxyethyl)formamides are synthesized in the same manner from a formamide and acetal, but it entails the same problems.

A process using an ethylidene biscarboxylic amide as the starting material is described in Japanese Unexamined Patent Publication Nos. 1-100153 and 2-304053. This process gives the desired N-(1-alkoxyethyl)carboxylic amide both easily and at a high yield by reacting an alkanol with an ethylidene biscarboxylic amide which can be easily produced from readily obtainable and low-cost acetaldehyde and carboxylic amides or from vinyl ether and carboxylic amides. However, among problems associated with this process is the need for a complicated procedure including extraction, in order to isolate the N-(1-alkoxyethyl) carboxylic amide after completion of the reaction, as well as the need for the two steps of synthesis of the ethylidene biscarboxylic amide and synthesis of the N-(1-alkoxyethyl)carboxylic amide.

A process using acetaldehyde as the starting material is described in Japanese Examined Patent Publication No. 6-17351 and Japanese Unexamined Patent Publication No. 63-96160. Despite a relatively high yield for the desired N-(1-alkoxyethyl)carboxylic amide, acetal and ethylidene bisacetamide by-products result. Japanese Examined Patent Publication No. 5-81581 describes a similar process. Here there is discussed the possibility recycling the acetal by-product for reuse in the reaction system during the production process for N-(1-alkoxyethyl)carboxylic amide, but no concrete disclosure is given regarding the reaction results. Also, the reaction results are not of a sufficient level.

On the other hand, Japanese Unexamined Patent Publication No. 6-100515 describes a process for producing a desired N-(1-alkoxyethyl)carboxylic amide at a relatively high yield in the presence of an acetal and ethylidene biscarboxylicamide.

Since the process using acetaldehyde in this manner allows synthesis of the desired N-(1-alkoxyethyl)carboxylic amide at a relatively high yield by single-step reaction from the 3 easily obtainable and inexpensive compounds carboxylic amide, acetaldehyde and alcohol in the presence of a strongly acidic catalyst, it is expected to be an industrially advantageous process for producing N-(1-alkoxyethyl) carboxylic amide.

Japanese Unexamined Patent Publication Nos. 62-289549 and 63-96160 disclose a process in which a desired N-(1-alkoxyethyl)acetamide is obtained at a high yield, by using an acetamide, acetaldehyde and an alcohol as the starting material, in the presence of an acidic catalyst. This process provides an advantage in that the reaction products and catalyst can easily be separated, since a strongly acidic ion-exchange resin of a heterogeneous catalyst is used.

However, when a strongly acidic ion-exchange resin is used, it may be inactivated during the use. This is supposed to be due to the presence of impurities such as a trace amount of basic ions by-produced during the reaction, metal ions or basic substances contained in the starting material, and the like. Therefore, this process is industrially unsatisfactory in the view point of the discontinuity of production due to the inactivation of the catalyst, the cost for regenerating the inactivated catalyst and the like.

Further, the above-mentioned Japanese Unexamined Patent Publication No. 6-100515 discloses the use of a homogeneous catalyst. However, the process includes a problem of disposal of the neutralized salt, since it is necessary to use a large amount of an acidic catalyst.

Incidentally, since all of these processes are equilibrium reactions, none can completely convert all of the carboxylic amide to N-(1-alkoxyethyl)carboxylic amide. Consequently, the carboxylic amide starting material is present in the reaction solution in addition to the N-(1-alkoxyethyl) carboxylic amide. Generally speaking, the N-(1-alkoxyethyl)carboxylic amide and its carboxylic amide starting material have very similar physical properties including vapor pressure, and their purification has been particularly difficult when the alkoxy groups are lower aliphatic alkoxy groups such as methoxy, ethoxy and isopropoxy.

When necessary, obtained N-(1-alkoxyethyl)carboxylic amides are subjected to thermal cracking or catalytic cracking reaction to accomplish alcohol elimination reactions, for production of N-vinylcarboxylic amides. This reaction also is an equilibrium reaction, and thus the N-(1-alkoxyethyl) carboxylic amide cannot be completely converted to N-vinylcarboxylic amide. Consequently, the resulting reaction solution contains the unreacted N-(1-alkoxyethyl) carboxylic amide and carboxylic amide as major impurities in addition to the N-vinylcarboxylic amide.

Various processes for recovery and purification of the N-vinylcarboxylic amide from the reaction solution have been proposed. For example, when the N-vinylcarboxylic amide is obtained in a crystallizing procedure, not all of the N-vinylcarboxylic amide can be recovered in principle, and the resulting mother liquor is composed of the N-(1-alkoxyethyl)carboxylic amide and carboxylic amide, which includes the N-vinylcarboxylic amide.

On the other hand, when the N-vinylcarboxylic amide is obtained by a separating procedure such as distillation or extraction, it is quite difficult to separate it because its physical properties are similar to those of the N-(1-alkoxyethyl)carboxylic amide and carboxylic amide. Consequently, in most cases there are obtained the recovered and purified N-vinylcarboxylic amide and a distilled fraction or extraction residue containing the N-(1-alkoxyethyl) carboxylic amide and carboxylic amide also containing the N-vinylcarboxylic amide.

Thus, recovery of such mixtures composed of N-(1-alkoxyethyl)carboxylic amides and carboxylic amides containing N-vinylcarboxylic amides as useful substances in an efficient and easy manner has been a problem.

As mentioned above, in conventional processes for synthesizing N-(1-alkoxyethyl)carboxylic amides, many improvements are necessary in terms of the yield, formation of by-products, difficulty in obtaining starting materials, catalyst life and complexity of the reaction and purification steps, and it has been difficult to obtain the N-(1-alkoxyethyl)carboxylic amides at high concentration with a low content of unreacted carboxylic amide.

In addition, even when an N-(1-alkoxyethyl)carboxylic amide is used for the production of an N-vinylcarboxylic amide, the method has not been satisfactory in terms of the yield, by-product control and complexity of the entire production process including the subsequent steps of recovery and purification.

SUMMARY OF THE INVENTION

It is an object of the present invention to develop an industrially advantageous process for producing N-(1-alkoxyethyl)carboxylic amides.

The present invention provides a process for efficient production of N-(1-alkoxyethyl)carboxylic amides both easily and at a satisfactory final yield, either by reacting an alcohol of 1–5 carbon atoms with an N-vinylcarboxylic amide in the presence of an acidic catalyst, or by utilizing an unreacted raw material, unreacted intermediate or unrecovered product for the synthesis of the N-(1-alkoxyethyl) carboxylic amide.

In other words, the present invention provides a process for producing N-(1-alkoxyethyl)carboxylic amides using alcohols of 1–5 carbon atoms and N-vinylcarboxylic amides as the starting materials, with further addition of a starting material which is at least one from among N-(1-alkoxyethyl) carboxylic amides, carboxylic amides, ethylidene biscarboxylic amides, acetals, acetaldehyde and water, and reacting these in the presence of an acidic catalyst.

The present invention also provides a process for producing N-(1-alkoxyethyl)carboxylic amides as mentioned above in which a water-soluble strong acid is added during the reaction of the starting material is reacted using a strongly acidic ion-exchange resin as the catalyst.

The present invention further provides a process for producing N-vinylcarboxylic amides characterized by comprising a first step of obtaining an N-(1-alkoxyethyl) carboxylic amide by the process described above, a second step of catalytic cracking or thermal cracking of the N-(1-alkoxyethyl)carboxylic amide of the first step to convert it to N-vinylcarboxylic amide, and a third step of obtaining purified N-vinylcarboxylic amide from the second step, wherein the remainder from the third step is recycled to the first step.

The present invention still further provides a process for producing an N-vinylcarboxylic amide homopolymer or copolymer using the obtained N-vinylcarboxylic amide as the monomer.

DESCRIPTION OF THE PREFERRED EMBODIMENTS

The process of the present invention will now be explained in more detail.

According to the invention, an aliphatic alcohol of 1–5 carbon atoms may be used as the alcohol. Examples include methanol, ethanol, n-propanol, isopropanol, n-butanol, sec-butanol and 1-pentanol, among which are preferred methanol, ethanol, isopropanol and n-butanol.

Examples of N-vinylcarboxylic amides include N-vinyl aliphatic carboxylic amides such as N-vinylformamide, N-vinylacetamide and N-vinylpropionamide, among which are preferred N-vinylformamide and N-vinylacetamide.

Examples of acetals include acetals derived from acetaldehyde and aliphatic alcohols such as methanol, ethanol, n-propanol, isopropanol, n-butanol, sec-butanol and 1-pentanol.

Since these acetals and alcohols are in an equilibrium reaction relationship and undergo exchange reaction of alkoxy groups under reaction conditions, combinations of the same types of alcohol and acetal, such as methanol and dimethylacetal or ethanol and diethylacetal, are preferred.

The carboxylic amide used may generally be an aliphatic carboxylic amide. Preferred ones include formamide, acetamide and propionamide, with formamide and acetamide being particularly preferred. These carboxylic amides are reacted with the acetaldehyde and alcohol and/or the acetal in the aforementioned production step, to give the desired N-(1-alkoxyethyl)carboxylic amide.

The ethylidene biscarboxylic amide may be, for example, an ethylidene biscarboxylic amide from an aliphatic carboxylic amide such as formamide, acetamide or propionamide, and ethylidene biscarboxylic amides from formamide and acetamide are particularly preferred. These ethylidene biscarboxylic amides are reacted with the alcohol and/or acetal in the aforementioned producing step, to give the desired N-(1-alkoxyethyl)carboxylic amide.

The N-(1-alkoxyethyl)carboxylic amide may be one having an alkoxy group of 1 to 5 carbon atoms and derived from an aliphatic carboxylic amide such as formamide, acetamide, propionamide, butyramide or isobutyramide, for example, N-(1-methoxyethyl)formamide, N-(1-methoxyethyl)acetamide, N-(1-methoxyethyl) propionamide, N-(1-ethoxyethyl)formamide, N-(1-ethoxyethyl)acetamide, N-(1-ethoxyethyl)propionamide, N-(1-isopropoxyethyl)formamide, N-(1-isopropoxyethyl) acetamide and N-(1-isopropoxyethyl)propionamide, among which are particularly preferred N-(1-alkoxyethyl) formamides and N-(1-alkoxyethyl)acetamides.

Since these substances having a carboxylic amide group are in an equilibrium reaction relationship and undergo exchange reaction of carboxylic amide groups under reaction conditions, combinations of the same types of N-(1- alkoxyethyl)carboxylic amide and carboxylic amide, such as N-(1-alkoxyethyl)acetamide and acetamide or N-(1-alkoxyethyl)formamide and formamide, are preferred.

The acidic catalyst used according to the invention may be either a homogeneous or non-homogeneous catalyst, and examples of the former include mineral acids such as hydrochloric acid, sulfuric acid, nitric acid, and phosphoric acid, heteropolyacids such as phosphotungstic acid and organic acids such as methanesulfonic acid and p-toluenesulfonic acid. Examples of the latter include gel and porous acidic ion-exchange resins, for example "DIAION SK-1B", "Ambalite IR-120B", "Dowex 50W", "Diaion PK-216", "Ambalite 200C", "Amberlist 15" and "Dowex MSC-1" (all registered trademarks). Among them, the acidic ion-exchange resins are industrially preferred.

The water-soluble strong acid added during the reaction with the use of the acidic ion-exchange resin as the catalyst is also not restricted so long as it is generally water-soluble and a strong acid, and examples thereof include mineral acids such as hydrochloric acid, sulfuric acid, nitric acid, and phosphoric acid, heteropolyacids such as phosphotungstic acid and organic acids such as methanesulfonic acid and p-toluenesulfonic acid.

Examples of the reactions associated with the production of N-(1-alkoxyethyl)carboxylic amide according to the present invention are shown by the following equations (1)–(8):

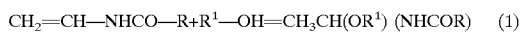
$$CH_2=CH-NHCO-R+R^1-OH=CH_3CH(OR^1) \ (NHCOR) \quad (1)$$

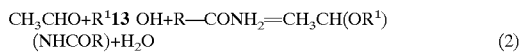
$$CH_3CHO+R^1\ ^{13}OH+R-CONH_2=CH_3CH(OR^1)(NHCOR)+H_2O \quad (2)$$

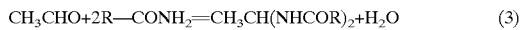
$$CH_3CHO+2R-CONH_2=CH_3CH(NHCOR)_2+H_2O \quad (3)$$

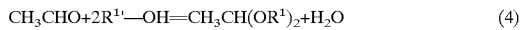
$$CH_3CHO+2R^{1'}-OH=CH_3CH(OR^1)_2+H_2O \quad (4)$$

$$CH_3CH(OR^1)\ (NHCOR)+R-CONH_2=CH_3CH(NHCOR)_2+R^1-OH \quad (5)$$

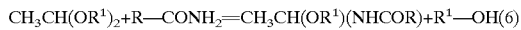
$$CH_3CH(OR^1)_2+R-CONH_2=CH_3CH(OR^1)(NHCOR)+R^1-OH \quad (6)$$

$$CH_2=CH-NHCO-R+R-CONH_2=CH_3CH(NHCOR)_2 \quad (7)$$

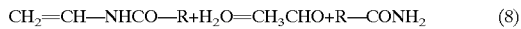
$$CH_2=CH-NHCO-R+H_2O=CH_3CHO+R-CONH_2 \quad (8)$$

in which R represents a hydrogen atom or an alkyl group of 1 to 3 carbon atoms and $R^1$ represents an alkyl group of 1 to 5 carbon atoms.

All of these reactions are equilibrium reactions. Therefore, the molar ratios of the starting materials used are determined by the desired reaction solution composition, i.e. the desired reaction results. Also, because equilibrium constants differ depending on the type of alcohol and carboxylic amide, the preferred molar ratio ranges will vary.

An important factor in determining the molar ratios for the starting materials is achieving an increase in the reaction results, i.e. the yield of the object compound, N-(1-alkoxyethyl)carboxylic amide, to improve the productivity, i.e. the concentration of the N-(1-alkoxyethyl)carboxylic amide in the reaction solution. Also, when an N-(1-alkoxyethyl)carboxylic amide, carboxylic amide, ethylidene biscarboxylic amide, acetal, acetaldehyde or water is used in the reaction starting material in addition to the N-vinylcarboxylic amide and alcohol, the by-products such as acetals and ethylidene biscarboxylic amides preferably undergo no fluctuation before and after the reaction. While these compounds are by-products, they contribute significantly to the equilibrium reaction. These by-products are generally separated as products after the reaction and recycled through the reaction process in order to help reduce waste and lower costs. Consequently, to maintain a continuously constant reaction, preferably no fluctuation occurs with the by-products. When the concentration of these by-products is lowered by the reaction, the reduced concentration of the by-products must be re-synthesized and added to the reaction starting material. Conversely, when the concentration of the by-products is increased by the reaction, the increase must be eliminated.

In light of these factors, the following molar ratios are usually preferred for each of the components in the starting material. The molar ratio of the N-vinylcarboxylic amide and alcohol may be selected within a range of 1:0.1–100, within which 1:0.5–25 is particularly preferred.

When an N-(1-alkoxyethyl)carboxylic amide, carboxylic amide, ethylidene biscarboxylic amide, acetal, acetaldehyde or water is also present, the molar ratios of the N-vinylcarboxylic amide and N-(1-alkoxyethyl)carboxylic amide, carboxylic amide, ethylidene biscarboxylic amide, acetal, acetaldehyde and water may be selected within the range of 1:0-20:0-20:0-10:0-200:0-50:0-10, within which 1:0.1-10:0.1-10:0.01-1:10-100:1-20:1-5 is particularly preferred.

No improvement in yield can be expected when the molar ratio of the acetaldehyde to the N-vinylcarboxylic amide, carboxylic amide or N-(1-alkoxyethyl)carboxylic amide is increased beyond this range, and production of acetaldehyde condensates merely increases. Yields are reduced at below this range. Yields of the N-(1-alkoxyethyl)carboxylic amide are reduced when the molar ratio of the alcohol to the N-vinylcarboxylic amide, carboxylic amide or N-(1-alkoxyethyl)carboxylic amide is above this range, while the acetal also increases and productivity is lowered. At below this range, the addition reaction of carboxylic amide to N-vinylcarboxylic amide is dominant, increasing the production of ethylidene biscarboxylic amide, and reducing the acetal. When the molar ratio of the acetal to the N-vinylcarboxylic amide, carboxylic amide or N-(1-alkoxyethyl)carboxylic amide is above this range, productivity is lowered while the amount of acetal is reduced. Also, at below this range the yield of N-(1-alkoxyethyl)carboxylic amide is lower and production of the ethylidene biscarboxylic amide increases. This range for the molar ratio of the ethylidene biscarboxylic amide to the N-vinylcarboxylic amide, carboxylic amide or N-(1-alkoxyethyl)carboxylic amide provides a balance for the amount of ethylidene biscarboxylic amide before and after the reaction. Also, water is preferably not added to the N-vinylcarboxylic amide, carboxylic amide or N-(1-alkoxyethyl)carboxylic amide beyond this range, since it results in a lower yield of N-(1-alkoxyethyl)carboxylic amide and reduced acetal.

These molar ratios of each of the components in the reaction starting material are defined for the purpose of the present invention. However, as already mentioned, the reactions according to the invention are all equilibrium reactions. These equilibrium reactions are also very complex reaction systems with interrelation between the reaction starting materials and products. Consequently, although the composition of the reaction starting material can also be discussed in terms of the molar ratios of each of the compounds, the "moieties" composing the compounds will now be analyzed and the starting material composition of the invention will be explained in terms of the proportion of "moieties".

According to the invention, a "moiety" is a functional group composing each of the compounds, of which there are 4 moieties, "ethylidene", "alkoxy", "amide" and "water".

For example, N-(1-alkoxyethyl)carboxylic amides comprise one "ethylidene" moiety, one "alkoxy" moiety and one "amide" moiety. Acetals comprise one "ethylidene" moieties and two "alkoxy" moieties. Acetaldehyde is considered in the following manner. As above, an acetal moiety comprises one "ethylidene" moiety and two "alkoxy" moieties. The two alcohol equivalents and water obviously are two "alkoxy" moieties and one "water" moiety, respectively. Therefore, as shown in Table 1 for the stoichiometric formula for the moieties, the acetaldehyde moiety becomes one "ethylidene" moiety and one "water" moiety.

| Stoichiometric formula: | | | | | | |
|---|---|---|---|---|---|---|
| | acetaldelyde | + | 2 alcohol | = acetal | + | H$_2$O |
| (number of moieties) | | | | | | |
| ethylidene | 1 | | 0 | 1 | | 0 |
| alkoxy | 0 | | 2 | 2 | | 0 |
| water | 1 | | 0 | 0 | | 1 |

The moieties constituting the other compounds are shown in Table 1 below, derived in the same manner.

TABLE 1

Moieties of related compounds

| Moiety | Acetaldehyde | Alcohol | Acetal | Carboxylic Amide | EA | NV | EBA | H$_2$O |
|---|---|---|---|---|---|---|---|---|
| Ethylidene | 1 | | 1 | | 1 | 1 | 1 | |
| Alkoxy | | 1 | 2 | | 1 | | | |
| Amide | | | | 1 | 1 | 1 | 2 | |
| Water | 1 | | | | | | | 1 |

"EA": N-(1-alkoxyethyl)carboxylic amide
"NV": N-vinylcarboxylic amide
"EBA": ethylidene biscarboxylic amide The starting material represented in terms of the proportion of "moieties" may be "amide":"ethylidene":"alkoxy":"water"=1:1-20:1-100:0-10, and preferably 1:5-15:10-50:1-5.

A batch or continuous reaction system is used. In the case of by a batch system, the starting materials and homogeneous catalyst or the starting materials, heterogeneous catalyst and water-soluble strong acid are supplied to a reactor. In the case of a continuous system, the starting materials and homogeneous catalyst are fed to a stirring vessel, or the starting materials and water-soluble strong acid are fed to a columnar reactor prefilled with the heterogeneous catalyst. The present invention has a greater effect when a continuous system is used with a catalyst-filled catalyst layer through which the starting material composition containing the water-soluble strong acid is passed.

The amount of catalyst may be appropriately selected within a range of 0.01–30 wt %, and preferably 0.05–15 wt % with respect to the weight of the starting material. There is no notable increase in the reaction rate if used at over 30 wt %, and this is therefore economically disadvantageous. At under 0.01 wt % the reaction rate is too slow, and therefore this is not preferred in terms of productivity.

The amount of the water-soluble strong acid where the strongly acidic ion-exchange resin is used as the catalyst may be selected within a range of $2\times10^{-3}$–$3\times10^{-1}$ equivalents per total moles of the carboxylic amide group-containing substances in the starting material, and $2\times10^{-3}$–$3\times10^{-2}$ equivalents is preferred, while $2\times10^{-3}$–$1\times10^{-2}$ equivalents is particularly preferred.

The equivalents referred to here represent the chemical equivalents used to indicate the amount of acid with respect to the carboxylic amide. Using more than $3\times10^{-2}$ equivalents is not advantageous since the life-extending effect on the catalyst is already saturated and no greater usable life extension can be expected, while it becomes impossible to avoid secondary production of the corresponding neutral salts proportional to the amount of strong acid used. Also, fewer than $2\times10^{-3}$ equivalents is not advantageous as no significant usable life-extending effect on the catalyst is exhibited.

The method of adding the water-soluble strong acid is not particularly restricted and may be a method whereby it is added beforehand to the starting material composition, or a method whereby it is added to the starting material composition just before contacting with the strongly acidic ion-exchange resin. In the latter case, the strong acid is preferably diluted before addition to prevent corrosion of the apparatus.

The diluent used for this purpose is not especially restricted so long as the strong acid dissolves uniformly therein, but in order to avoid altering the composition of the reaction starting material, it is preferably the same substance used as the starting material. Specifically, it may be any of the aforementioned alcohols of 1–5 carbon atoms or acetals. Addition of a small amount of water is effective for minimizing undesirable reactions such as degeneration of the strong acid.

The reasons for the extended life of the strongly acidic ion-exchange resin in the reaction are not fully understood, but it is believed that metal ions produced by corrosion of the apparatus by the extremely trace basic substances in the starting material or acidic components in the starting material, or extremely trace basic ions produced by hydrolysis of the carboxylic amide starting material or solvolysis reaction during the reaction, are adsorbed onto the strongly acidic ion-exchange resin causing inactivation, and that this is suppressed by addition of the small amount of water-soluble strong acid, thus having the effect of minimizing inactivation of the catalyst.

The reaction temperature may normally be selected within a range of 0–150° C., and more preferably 20–80° C. A temperature of under 0° C. is not preferred because the reaction rate is slowed. A temperature of over 150° C. is also not preferred because production of impurities is increased.

The reaction time will differ depending on the amount of catalyst used for the reaction, but it may normally be selected within a range of 0.05–10 hours, and preferably 0.1–5 hours.

The ideal reaction conditions will differ depending on the types of starting substances such as alcohol and acetal used, and thus it is important to establish the starting material composition, reaction temperature and reaction time within the above-mentioned ranges in a manner suited for a reaction with a favorable yield of the desired N-(1-alkoxyethyl)carboxylic amide. The pressure conditions may be reduced pressure, normal pressure or applied pressure, but normal pressure is usually adequate.

The second step, wherein the N-(1-alkoxyethyl) carboxylic amide obtained in the first step described above is subsequently subjected to catalytic cracking or thermal cracking for conversion to an N-vinylcarboxylic amide and alcohol, will now be explained.

The conversion of the N-(1-alkoxyethyl)carboxylic amide to the N-vinylcarboxylic amide is accomplished by a publicly known process such as thermal cracking or catalytic cracking. The reaction conditions may be, for example, in gaseous or liquid phase with a reaction temperature of 60–600° C., a reaction time of 0.3 seconds to 2 hours and a reaction pressure of 0.1 mmHg to atmospheric pressure. The catalyst used for catalytic cracking may be an alkali metal salt of a carboxylic acid, such as potassium acetate, or an alkali metal or alkaline earth metal oxide such as magnesium oxide.

An embodiment of the third step, wherein a purified N-vinylcarboxylic amide is obtained from the solution of step 2, will now be explained.

According to the process of the invention, the thirst step may be according to a publicly known method such as precision distillation, azeotropic distillation, recrystallization or pressure crystallization.

There are no particular restrictions on the distillation apparatus for separation by precision distillation, and a rack tray column or packed column may be used which has 1–50 theoretical levels; however, the precision distillation column used preferably has low pressure loss and excellent precision distillation performance, an example of one being a packed column with an ordinary packing substance. Since N-vinylcarboxylic amides readily undergo degeneration by heat, the distillation is preferably carried out at as low a temperature as possible. Therefore, distillation is performed under a pressure of 0.01 to 100 mmHg.

The present invention may be carried out either continuously or non-continuously, but a continuous procedure is preferred for reasons of productivity and operation stability. The reflux ratio is not particularly restricted and may be set in harmony with the N-vinylcarboxylic amide content and type and the performance of the distillation column, but a ratio of about 0.1–20 is sufficient, and about 0.5–10 is preferred.

According to the process of the invention, when separation is accomplished by recrystallization through cooling of the N-vinylcarboxylic amide solution, the solution may be cooled directly, but a recrystallization solvent with no reactivity and suitable solubility for the N-vinylcarboxylic amide may also be used. Examples of such recrystallization solvents include aromatic hydrocarbons such as benzene, toluene and xylene, aliphatic hydrocarbons such as pentane, cyclopentane, hexane, cyclohexane and heptane, alcohols such as methanol, ethanol, n-propyl alcohol, isopropyl alcohol, n-butanol, isobutanol, sec-butanol, tert-butanol and cyclohexanol, halogenated hydrocarbons such as methylene chloride, chloroform and chlorbenzene, ketones such as acetone, methyl ethyl ketone and cyclohexanone, esters such as methyl acetate, ethyl acetate, propyl acetate and butyl acetate, ethers such as diethyl ether, amides such as N,N-dimethylformamide and N,N-dimethylacetamide, and dimethylsulfoxide, among which are particularly preferred toluene, cyclohexane, methanol and isopropyl alcohol. Combinations of these may also be used. The appropriate cooling temperature will depend on the types and amounts of the N-vinylcarboxylic amide and recrystallization solvent, but is generally −20–50° C., and preferably −10–40° C.

The crystallizing apparatus used according to the invention may be either a continuous or batch type, and the crystallizing method may be by heat exchange with a cooling medium or condensation and cooling by evaporation of the solvent, while there are also no restrictive conditions on the type of structure.

There are also no restrictions on the separating apparatus used for the crystals for the invention, and it may be either a vacuum or pressurized type, based on gravity or centrifugal force.

According to the invention, a solid/liquid separating apparatus may also be used to accomplish the crystallizing procedure and separating procedure in the same apparatus. Preferred examples thereof include, for example when no recrystallizing solvent is used, a pressure crystallizer, or a falling-film crystallizer (e.g. MWB sorting crystallizer) or column-type continuous crystallizing purifier (e.g. BMC apparatus). When high-density slurry is filtered, an automatic Nutsche filter, such as a Rosenmund filter is preferred.

Primarily the N-vinylcarboxylic amide, N-(1-alkoxyethyl)carboxylic amide and carboxylic amide are present in the residue from purification and separation of the N-vinylcarboxylic amide in the third step.

According to the invention, this mixture is recycled back to the first step and used as starting material for synthesis of the N-(1-alkoxyethyl)carboxylic amide. The residue may be recycled directly, but when high-boiling substances such as N-vinylcarboxylic amide oligomers are present, they may be used for the reaction after undergoing distillation purification.

The compounds obtained by the process of the invention are primarily intermediates for production of N-vinylcarboxylic amides, for example, and as mentioned at the beginning, they are also used to derive homopolymers, copolymers and other useful chemicals.

N-vinylcarboxylic amides obtained according to the present invention may be used as monomers for the production of high-molecular-weight N-vinylcarboxylic amide homopolymers or copolymers with other copolymerizable monomers.

The following are concrete representative examples of monomers which are copolymerizable with N-vinylcarboxylic amides according to the invention.

Acrylic acid, methacrylic acid (hereunder collectively referred to as (meth)acrylic acid) and their sodium, potassium and other alkali metal salts; methyl ester, ethyl ester, propyl ester, butyl ester, pentyl ester, hexyl ester, heptyl ester, octyl ester, nonyl ester, decyl ester, stearyl ester, palmityl ester and other alkyl esters thereof; hydroxyethyl ester, hydroxypropyl ester, hydroxybutylester and other hydroxy lower alkyl esters thereof; dimethylaminomethyl ester, dimethylaminoethyl ester, dimethylaminopropyl ester, dimethylaminobutyl ester, diethylaminomethyl ester, diethylaminoethyl ester, diethylaminopropyl ester, diethylaminobutyl ester and other lower alkyl esters thereof substituted with lower alkyl amino groups; trimethylammonioethyl ester halide, trimethylammoniopropyl ester halide, triethylammonioethyl ester halide, triethylammoniopropyl ester halide and other lower alkyl ester halides thereof substituted with quaternary ammonium groups (the halide being preferably chloride or bromide); amides thereof;

dimethylaminomethylamide, dimethylaminoethylamide, dimethylaminopropylamide, dimethylaminobutylamide, diethylaminomethylamide, diethylaminoethylamide, diethylaminopropylamide, diethylaminobutylamide and other lower alkyl amides thereof substituted with lower alkyl amino groups; trimethylammonioethylamide halide, trimethylammoniopropylamide halide, triethylammonioethylamide halide, triethylammoniopropylamide halide and other lower alkylamide halides thereof substituted with quaternary ammonium groups; sulfomethylamide, sulfoethylamide, sulfopropylamide, sulfobutylamide, sodium sulfomethylamide, sodium sulfoethylamide, sodium sulfopropylamide, sodium sulfobutylamide, potassium sulfomethylamide, potassium sulfoethylamide, potassium sulfopropylamide, potassium sulfobutylamide and other lower alkyl amides thereof substituted with sulfonic acid or alkali metal sulfonic acid; acrylonitrile; methyl vinyl ether, ethyl vinyl ether, propyl vinyl ether, butyl vinyl ether and other vinyl ethers; methyl vinyl ketone, ethyl vinyl ketone and other vinyl ketones; vinyl acetate, vinyl propionate and other lower vinyl 4- carboxylates; maleic anhydride, maleic acid, sodium malate, potassium malate, etc.

Among these are particularly preferred (meth)acrylic acid, sodium (meth)acrylate, methyl (meth)acrylate, ethyl (meth)acrylate, propyl (meth)acrylate, butyl (meth)acrylate, 2-hydroxyethyl (meth)acrylate, 2-hydroxypropyl (meth) acrylate, 2-hydroxybutyl (meth)acrylate, dimethylaminoethyl (meth)acrylate, trimethylchloride aminoethyl (meth) acrylate, acrylamide, sulfopropylacrylamide, sulfobutylacrylamide, sodium sulfopropylacrylamide, sodium sulfobutylacrylamide, acrylonitrile, methyl vinyl ether, ethyl vinyl ether, methyl vinyl ketone, ethyl vinyl ketone, vinyl acetate, N-vinyl-2-pyrrolidone and maleic anhydride.

In addition, crosslinkable monomers and crosslinking agents which are compounds having 2 or more unsaturated groups per molecule may also be used as the monomer copolymerizable with the N-vinylcarboxylic amide of the invention.

The polymerization process is not necessarily restricted, and any conventional publicly known process may be employed. Normally, a solution polymerization, reverse-phase suspension polymerization or reverse-phase emulsion polymerization process is preferred.

An example of a solution polymerization process is one in which the monomer components and crosslinking agent are uniformly dissolved in water, an organic solvent or a mixed solvent, the dissolved oxygen in the system is eliminated by vacuum degassing or substitution with an inactive gas such as nitrogen or carbon dioxide gas, and then a polymerization initiator is added to induce the reaction. The polymerization initiation temperature is usually about −10–60° C., with a reaction time of about 1–10 hours.

Examples of the invention will now be provided, with the understanding that the invention is not limited to these examples.

EXAMPLE 1

After adding 1 kg of N-vinylacetamide, 3 kg of methanol and 30 g of the strongly acidic ion-exchange resin "Dowex MSC-1" (registered trademark) to a 5 L glass reactor, the mixture was stirred at room temperature for 5 hours. Analysis of the reaction solution indicated quantitative production of N-(1-methoxyethyl)acetamide.

EXAMPLE 2

A mixture was prepared containing 19.1 g of a mixture comprising 6.9 wt % acetamide, 57.4 wt % N-vinylacetamide and 35.6 wt % N-(1-methoxyethyl) acetamide (hereunder referred to as "NVA mixture"), 726.5 g of a mixture comprising 96.0 wt % dimethylacetal, 0.1 wt % acetaldehyde, 2.9 wt % methanol, 0.23 wt % water and 0.27 wt % hemiacetal (hereunder referred to as "acetal starting material"), 86.7 g of acetaldehyde, 126.7 g of methanol, 27.8 g of acetamide, 6.8 g of N-vinylacetamide and 9.9 g of water. The molar ratio of the N-vinylacetamide and the N-(1-methoxyethyl)acetamide, acetamide, acetal, acetaldehyde, water and methanol in the mixture was 1:0.36:2.4:37.2:9.7:3.1:22.3. In terms of "moieties" the proportion was "amide":"ethylidene":"methoxy":"water"= 1:12.9:26.0:3.4. The components were thoroughly mixed to prepare the reaction starting solution, and 50 ml thereof was fed each hour through the top of a reaction column with an inner diameter of 25 mm filled with 10 ml of the strongly acidic ion-exchange resin "Dowex MSC-1" (registered trademark). Warm water at 40° C. was poured over the jacket of the reactor to maintain a reaction temperature of 40° C. The reaction results were calculated based on quantitative analysis by gas chromatography, after neutralization of the reaction solution obtained through the outlet at the bottom of the reactor. Based on the reaction results after 7 hours, the N-(1-methoxyethyl)acetamide yield (with respect to acetamide+N-(1-methoxyethyl)acetamide+N-vinylacetamide) was 87.4%, and the ethylidene bisacetamide yield as a reaction by-product (calculated on the same standard as the N-(1-methoxyethyl)acetamide yield) was 5.2%.

EXAMPLE 3

A mixture was prepared containing 11.5 g of NVA mixture, 435.9 g of acetal starting material, 50.6 g of acetaldehyde, 76.0 g of methanol, 14.8 g of acetamide, 6.7 g of N-vinylacetamide and 6.5 g of water. The molar ratio of the N-vinylacetamide and the N-(1-methoxyethyl) acetamide, acetamide, acetal, acetaldehyde, water and methanol in the mixture was 1:2.89:1.7:29.8:7.54:2.68:17.9. In terms of "moieties" the proportion was "amide":"ethylidene":"methoxy":"water" 1:12.9:26.0:3.4. The components were thoroughly mixed and used as a reaction starting material for reaction in the same manner as Example 2, and based on the reaction results after 7 hours, the N-(1-methoxyethyl)acetamide yield was 87.5% and the ethylidene bisacetamide yield as a reaction by-product was 5.4%.

EXAMPLE 4

A starting material composition was prepared with a molar ratio of N-vinylacetamide, N-(1-methoxyethyl) acetamide, acetamide, acetaldehyde dimethylacetal, acetaldehyde, water and methanol of 1:0.3:0.2:17.3:5.4:2.2:10.3. In terms of "moieties" the proportion was "amide":"ethylidene":"methoxy":"water"= 1:14.1:26.4:4.5. Sulfuric acid was further added to the starting material in an amount of 3.76×10-3 equivalents based on the total moles of N-vinylacetamide, N-(1-methoxyethyl)acetamide and acetamide and upon thorough dissolution a reaction starting solution was obtained.

The reaction starting solution was fed at 50 ml per hour to the upper portion of a catalyst-filled column (reactor) with an inner diameter of 25 mm which had been filled with 10 ml of the strongly acidic ion-exchange resin "Dowex MSC-1" (registered trademark). Warm water at 40° C. was poured over the jacket of the reactor to maintain a reaction temperature of 40° C. The reaction results in terms of production of N-(1-methoxyethyl)acetamide were calculated based on quantitative analysis by gas chromatography after neutralization of the reaction solution obtained through the lower outlet of the reactor.

Based on reaction results after 24 hours, the acetamide conversion rate was 93.5% and the N-(1-methoxyethyl) acetamide selectivity was 96.3%.

Based on reaction results after 650 hours, the acetamide conversion rate was 93.2% and the N-(1-methoxyethyl) acetamide selectivity was 96.1%, demonstrating that no reduction in activity occurred. If the activity reduction is defined as the reduction in acetamide conversion rate at a given time with respect to the acetamide conversion rate at the start of reaction, then the activity reduction after 650 hours was 0.32%. Production of ethylidene bisacetamide by-product was 2.8%.

EXAMPLE 5

Exactly the same procedure was conducted as in Example 4, except that the addition of $3.76 \times 10^{-3}$ equivalents of sulfuric acid in Example 4 was changed to $1.88 \times 10^{-2}$ equivalents. Based on reaction results after 24 hours, the acetamide conversion rate was 93.1% and the N-(1-methoxyethyl)acetamide selectivity was 95.8%. Based on reaction results after 650 hours, the acetamide conversion rate was 92.9% and the N-(1-methoxyethyl)acetamide selectivity was 95.2%, for an activity reduction of 0.21%. Production of ethylidene bisacetamide by-product was 3.2%.

EXAMPLE 6

The starting material composition was prepared in the same manner as Example 4, but ⅕ of the methanol in the starting material was taken separately and combined with sulfuric acid in an amount of $3.76 \times 10^{-3}$ equivalents based on the total moles of N-vinylacetamide, N(1-methoxyethyl)acetamide and acetamide, and thoroughly dissolved.

The same procedure as in Example 4 was then. followed, except that the 2 solutions were fed separately to the reactor. Based on reaction results after 24 hours, the acetamide conversion rate was 92.9% and the N-(1-methoxyethyl) acetamide conversion rate was 90.0%. Based on reaction results after 650 hours, the acetamide conversion rate was 92.5% and the N-(1-methoxyethyl)acetamide selectivity was 89.9%, for an activity reduction of 0.43%. Production of ethylidene bisacetamide by-product was 4.7%.

Also, based on reaction results after 2000 hours, the acetamide conversion rate was 92.1% and the N-(1-methoxyethyl)acetamide selectivity was 91.6%, for an activity reduction of 0.86%. Production of ethylidene bisacetamide by-product was 5.0%.

EXAMPLE 7

First Step (Synthesis of N-(1-methoxyethyl)acetamide)

To 7869 kg of a recovered acetal solution comprising 74.4 wt % dimethylacetal, 13.8 wt % methanol, 7.5 wt % acetaldehyde, 3.3 wt % methyl acetate and 1 wt % water obtained in the water separation step described below and 144 kg of methanol obtained in the N-vinylacetamide concentration step described below, there was added an additional 15 kg of methanol, and then 212 kg of recycled solution comprising 11.0 wt % acetamide, 54.4 wt % N-vinylacetamide, 32.2 wt % N-(1-methoxyethyl)acetamide and 2.4 wt % of other components obtained by the filtrate recovery step described below, 239 kg of acetamide and 165 kg of acetaldehyde were added thereto and thoroughly mixed to prepare a reaction starting solution. The molar ratio of the N-vinylacetamide and the N-(1-methoxyethyl) acetamide, acetamide, acetal, acetaldehyde, water and methanol in the mixture was 1:0.28:3.14:46.4:12.3:3.64:27.8. In terms of "moieties" the proportion was "amide":"ethylidene":"methoxy":"water"= 1:13.2:26.6:3.5. Of this starting material, 450 L was fed each hour through the top of a reactor filled with 150 L of the strongly acidic ion-exchange resin "Dowex MSC-1" (registered trademark). Warm water at 40° C. was poured over the jacket of the reactor to maintain a reaction temperature of 40° C. The reaction results were calculated based on quantitative analysis by gas chromatography, after neutralization of the reaction solution obtained through the outlet at the bottom of the reactor. Based on the reaction results, the N-(1-methoxyethyl)acetamide yield (with respect to acetamide+N-(1-methoxyethyl)acetamide+N-vinylacetamide) was 88.0%, and the ethylidene bisacetamide yield as a reaction by-product (calculated on the same standard as the N-(1-methoxyethyl)acetamide yield) was 4.0%.

Acetal recovery step

In this step, the lighter boiling portion including dimethylacetal, methanol, acetaldehyde, methyl acetate and water was distilled off from the reaction solution obtained in the first step (synthesis of N-(1-methoxyethyl)acetamide). A 450 L portion of the reaction solution obtained in the first step (synthesis of N-(1-methoxyethyl)acetamide) was fed each hour to a falling-film continuous evaporator at a reduced pressure of 150 mmHg and a heating surface area of 2.8 $m^2$. Hot medium at 100° C. was circulated in the jacket. An evaporation residue was obtained which comprised N-(1-methoxyethyl)acetamide containing 2.6 wt % ethylidene bisacetamide and 4.4 wt % acetamide. The condensed solution from the volatilized portion comprising 72.9 wt % dimethylacetal, 13.5 wt % methanol, 7.4 wt % acetaldehyde, 3.2 wt % methyl acetate and 2.9 wt % water was later supplied to the water separation step described below.

Ethylidene bisacetamide separation step

The evaporation residue composed mainly of the N-(1-methoxyethyl)acetamide obtained in the acetal recovery step was subjected to simple distillation at 5 mmHg. Acetamide was present in the N-(1-methoxyethyl)acetamide in the resulting fraction at 4.1 wt %. This solution was then supplied to the second step (synthesis of N-vinylacetamide). The major component of the evaporation residue was ethylidene bisacetamide.

Second step (synthetic of N-vinylacetamide)

The fraction composed mainly of N-(1-methoxyethyl) acetamide obtained in the ethylidene bisacetamide separation step was fed at 33 g/min to a stainless steel reaction column with an inner diameter of 20 mm and a total length of 6 m, which had been heated to 440° C. and reduced to a pressure of 100 mmHg. A mixture of N-vinylacetamide and methanol produced by the thermal cracking reaction was condensed and recovered at a cooler provided at the outlet of the reaction column. The conversion rate of the N-(1-methoxyethyl)acetamide was 88%.

N-vinylacetamide concentration step

The reaction solution obtained in the second step (synthesis of N-vinylacetamide) was depressurized from 76 mmHg to 24 mmHg while distilling off the methanol. The residue from distillation contained 78.0 wt % N-vinylacetamide, 14.6 wt % N-(1-methoxyethyl) acetamide, 5.4 wt % acetamide and 2 wt % of other components.

Third step (purification of N-vinylacetamide)

The crude N-vinylacetamide solution obtained in the N-vinylacetamide concentration step was cooled to 28° C., partially crystallizing the N-vinylacetamide, to produce a slurry. The N-vinylacetamide slurry was subjected to 1800 kg/$cm^2$ pressure in a high-pressure container for pressure crystallization of the N-vinylacetamide while separating the mother liquor. The N-vinylacetamide crystal purity was 99.5%, and the mother liquor composition was 11.1 wt % acetamide, 4.9 wt % N-vinylacetamide, 29.9 wt % N-(1-methoxyethyl)acetamide and 4.1 wt % of other components.

Filtrate recovery step

The mother liquor obtained in the third step (N-vinylacetamide purification step) was subjected to simple distillation at 4 mmHg, and a distillate comprising 11.0 wt % acetamide, 54.4 wt % N-vinylacetamide, 32.2 wt % N-(1-methoxyethyl)acetamide and 2.4 wt % of other components was obtained at a yield of 90%. The resulting solution was supplied to the N-(1-methoxyethyl)acetamide synthesis step for recycling.

Water separation step

The distillate from the acetal recovery step comprising 72.9 wt % dimethylacetal, 13.5 wt % methanol, 7.4 wt % acetaldehyde, 3.2 wt % methyl acetate and 2.9 wt % water was fed at 200 L per hour to the center of a packed column with an inner diameter of 400 mm and a packed height of 10 m. The reflux ratio was 2, and heating was carried out to maintain a temperature of 60° C. at the top of the column and a temperature of 100° C. at the bottom of the column. The bottoms consisted of essentially water, and the distillate was a mixture comprising 74.4 wt % dimethylacetal, 13.8 wt % methanol, 7.5 wt % acetaldehyde, 3.3 wt % methyl acetate and 1 wt % water.

EXAMPLE 8

After adding and dissolving 745 g of water, 250 g of the N-vinylacetamide obtained in Example 7 and 0.409 g of N,N'-(diacetal)-N,N'-(divinyl)-1,4-bis(aminomethyl) cyclohexane as a crosslinking agent in a glass reactor and eliminating the dissolved oxygen with nitrogen gas, 0.075 g of 2,2'-azobis-2-(2-imidazolin-2-yl)propane dihydrochloride dissolved in 5 mL of deaerated water was added as a polymerization initiator, and the mixture was allowed to stand in a thermally insulated state. After 7 hours, the internal temperature of the reactor had reached 71° C. by heat of polymerization.

The present invention provides a process for producing N-(1-alkoxyethyl)carboxylic amides by reacting an alcohol of 1–5 carbon atoms with an N-vinylcarboxylic amide in the presence of an acidic catalyst, or with a further addition of at least one of N-(1-alkoxyethyl)carboxylic amides, carboxylic amides, ethylidene biocarboxylic amides, acetals, acetaldehyde and water.

In addition, the present invention provides a process for producing N-(1-alkoxyethyl)carboxylic amide by conducting the reaction with addition of a water-soluble strong acid to the starting material composition during the reaction using a strongly acidic ion-exchange resin as the catalyst.

The present invention further provides a process for producing N-vinylcarboxylic amide homopolymers and copolymers using the obtained N-vinylcarboxylic amides as monomers.

As a result, the yield of N-(1-alkoxyethyl)carboxylic amide is satisfactory through the entire production process including the subsequent recovery and purification steps and the production of by-products is minimized.

In addition, by using a strongly acidic ion-exchange resin as the catalyst, the catalyst maintains a high conversion rate and high selectivity, and this allows increased productivity and stable long-term production by vastly delaying the interval required for replacement of the strongly acidic ion-exchange resin.

We claim:

1. A process for producing an N-vinylcarboxylic amide, comprising (1) obtaining an N-(1-alkoxyethyl)carboxylic amide, (2) catalytically cracking or thermally cracking the N-(1-alkoxyethyl)carboxylic amide obtained to convert it to an N-vinylcarboxylic amide, and (3) purifying the N-vinylcarboxylic amide of (2), wherein the remainder from (3) is recycled to the (1).

* * * * *